United States Patent [19]
Takahashi et al.

[11] Patent Number: 5,948,825
[45] Date of Patent: *Sep. 7, 1999

[54] MICROEMULSION PREPARATION CONTAINING A SLIGHTLY ABSORBABLE SUBSTANCE

[75] Inventors: Masao Takahashi; Hiroshi Matsushita, both of Tokyo, Japan

[73] Assignee: Institute for Advanced Skin Research Inc., Kanagawa-ken, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/537,676

[22] PCT Filed: Apr. 19, 1994

[86] PCT No.: PCT/JP94/00645

§ 371 Date: Oct. 19, 1995

§ 102(e) Date: Oct. 19, 1995

[87] PCT Pub. No.: WO94/23749

PCT Pub. Date: Oct. 27, 1994

[30] Foreign Application Priority Data

Apr. 19, 1993 [JP] Japan ..................................... 5-91438

[51] Int. Cl.$^6$ .................................................. A61K 9/107

[52] U.S. Cl. .......................... 514/937; 514/807; 514/808

[58] Field of Search .................................. 424/434, 85.1, 424/85.2, 85.4, 85.5, 85.6, 85.7; 514/807, 808, 937; 530/303, 307, 315, 380; 930/60, 90, 140, 145, 150, DIG. 560, DIG. 660, DIG. 670

[56] References Cited

U.S. PATENT DOCUMENTS

| | | | |
|---|---|---|---|
| 4,731,384 | 3/1988 | Dell et al. | 514/658 |
| 4,931,210 | 6/1990 | Takahashi et al. | 252/314 |
| 5,037,653 | 8/1991 | Dawson | 424/405 |
| 5,281,580 | 1/1994 | Yamamoto et al. | |
| 5,496,811 | 3/1996 | Aviv et al. | 514/78 |
| 5,576,016 | 11/1996 | Amselem et al. | 424/450 |
| 5,662,932 | 9/1997 | Amselem et al. | 424/450 |
| 5,716,637 | 2/1998 | Anselem et al. | 4/450 |

FOREIGN PATENT DOCUMENTS

| | | |
|---|---|---|
| 135171-A2 | 3/1985 | European Pat. Off. . |
| 0152945 | 8/1985 | European Pat. Off. . |
| 366277-A2 | 5/1990 | European Pat. Off. . |
| 0610502 | 9/1992 | European Pat. Off. . |
| 9218147 | 10/1992 | WIPO . |
| 9302664 | 2/1993 | WIPO . |
| 9302665 | 2/1993 | WIPO . |
| 9305805 | 4/1993 | WIPO . |
| 9408603 | 4/1994 | WIPO . |
| 9408605 | 4/1994 | WIPO . |
| 9419001 | 9/1994 | WIPO . |

*Primary Examiner*—Robert H. Harrison
*Attorney, Agent, or Firm*—Browdy and Neimark

[57] ABSTRACT

Microemulsion preparation in which a plurality of specified surfactants are combined such that aqueous-phase droplets that contain a physiologically active substance of low absorption and which have an average size of 0.4–100 nm are dispersed in an oil-phase dispersion medium. In order to improve its low transdermic or transmucosal absorbability, the physiologically active substance is allowed to be present as dissolved in the aqueous-phase droplets in the W/O emulsion. The preparation is low in local irritation and uses neither malodorous substances such as higher alcohols nor conventional absorption enhancers.

5 Claims, No Drawings

# MICROEMULSION PREPARATION CONTAINING A SLIGHTLY ABSORBABLE SUBSTANCE

TECHNICAL FIELD

This invention relates to a microemulsion preparation that contains a physiologically active substance such as a high-molecular weight peptide which inherently can not be easily absorbed through the skin or mucous membrance but which is incorporated in such a way that its absorption through the skin or mucous membrance is improved.

BACKGROUND ART

The preparation of microemulsions is one attempt that has been made to improve the absorption of physiologically active substances through the skin or mucous membrane.

Microemulsions have been proposed that use alcohols such as octanol and butanol. However, they are not particularly suitable for oral administration since the alcohols they use have malodors. If microemulsions are prepared using large amounts of ionic surfactants, they are irritant to the mucous membrane and skin.

Peptides such as insulin and calcitonin have low absorbability through the mucous membrane. With a view to dealing with this problem, the use of absorption enhancers such as bile salts has been attempted but they have been found to damage or destroy epithelial cells of the mucous membrane.

DISCLOSURE OF INVENTION

An object of the invention is to prepare a microemulsion that is less irritating to the mucous membrane and skin and which uses neither malodorous higher alcohols such as butanol and octanol nor conventional absorption enhancers such as bile salts that will damage epithelial cells. It is another object of the invention to improve the absorption of certain physiologically active substances through the skin or mucous membranes by means of preparing such microemulsions.

The invention provides a microemulsion preparation that successfully solves the aforementioned problems of the prior art by combining at least two specified surfactants.

The surfactants to be used in the invention are selected from the following three classes (a), (b) and (c), among which a surfactant in class (c) is essential and combined with a surfactant in either one of classes (a) and (b). The surfactants in the respective classes are as follows:

(a) an ionic surfactant:
  di-2-ethylhexylsulfosuccinic acid sodium; and
  sodium alkylsulfate (the alkyl moiety has 8–20, preferably 10–14, carbon atoms);

(b) a nonionic surfactant with an HLB of 10–20:
  a polyoxyethylene hardened or unhardened castor oil (oxyethylene is added in 30–80, preferably 40–60, moles on average);
  an ester of polyethylene glycol and higher aliphatic acid (the aliphatic acid is a saturated or unsaturated aliphatic acid having 16–20, preferably 18, carbon atoms and ethylene glycol is added in 10–40 moles on average); and
  a polyoxyethylene alkyl ether (the alkyl moiety has 8–14, preferably 12, carbon atoms and oxyethylene is added in 4–25 moles on average); and (c) a nonionic surfactant with an HLB of 3–7:
  a mono- or polyglycerin aliphatic acid ester (the aliphatic acid is a saturated or unsaturated aliphatic acid having 16–20, preferably 18, carbon atoms and it is added in 1–2 moles per mole of glycerin, which is added in 0–4 moles);
  a sorbitan aliphatic acid ester (the aliphatic acid is a saturated or unsaturated aliphatic acid having 16–20, preferably 16–18, carbon atoms and added in 1–3 moles); and
  a polyoxyethylene hardened or unhardened castor oil (oxyethylene is added in 3–20, preferably 8–12, more preferably 10, moles on average).

The dispersion media that can be used in the invention are fats or oils that are not irritating to the skin or mucous membranes and which are liquid at room temperature or dissolve when heated by the body temperature to become liquid. Specific examples that may be used include edible vegetable or animal oils (aliphatic acid glycerin esters) such as soybean oil, sesame oil and olive oil; saturated or unsaturated aliphatic acids; and mono-, di- or triglycerin esters of middle-chain aliphatic acids ($C_6$–$C_{18}$).

The microemulsion of the invention can be prepared by a conventionally known method as follows.

A suitable combination of surfactants is added to an oil component as a dispersion medium and the ingredients are agitated and mixed thoroughly to prepare a uniform oily mixture. When the oil component is solid at room temperature, it is heated to melt the oil component before the surfactants are added and mixed. An active ingredient, or a physiologically active substance, such as calcitonin, erythropoietin or other peptide is dissolved in water.

The thus prepared aqueous solution of the physiologically active substance is added to the separately prepared oily mixture under agitation. Further agitation yields a microemulsion as a clear liquid. If necessary, an additional amount of the oil component may be added to adjust the concentration of the active ingredient.

The microemulsion thus obtained has dispersed droplets in sizes of 0.4–100 nm, preferably 1–100 nm, and hence is very stable.

If desired, albumin, glycerin, glycol and any other stabilizers may be incorporated in the aqueous phase.

The physiologically active substances of low absorbability through the skin or mucous membrane that can be applied in the invention include peptide drugs such as vasopressin, calcitonin, erythropoietin, colony stimulating factor, interleukins, interferons, insulin and accessory thyroid hormone, as well as slightly absorbable low-molecular weight ($\leqq 1,000$) drugs. Such low-molecular weight drugs are exemplified by the following:

(1) antibiotics: aclarubicin HCl, oxytetracrycline HCl, cefotiam HCl, carbenicillin sodium, cefmetazole sodium, etc.;
(2) antiarrythmics: procainamide HCl, disopyramide phosphate, lidocaine HCl, etc.:
(3) cardiotonics: etilefrine HCl, dopamine HCl, etc.;
(4) vasodilators: trapidil, etc.:
(5) local anesthetics: oxybuprocaine HCl, dibucaine HCl, procaine HCl, etc.;
(6) antitumors: bleomycin HCl, cytarabine, procarbazine HCl, cisplatin, vinblastine HCl, neocarzinostatin, doxorubicin HCl, etc.;
(7) agents acting on the autonomic nerve system: distigmine bromide, bethanechol chloride, propantheline bromide, etc.;
(8) antipyretic, analgesic antiinflammatories: antipyrine, tiaramide HCl, diclofenac sodium, etc.;
(9) agents acting on psychic nerves: imipramide HCl, clomipramine HCl, tiodaline HCl, flurazepam HCl, chlorpromazine HCl, levomepromazine HCl, etc.;

(10) narcotic analgesic/antitussive agents: oxycodone HCl, etc.;
(11) antispasmodics: cyclopentolate, etc.;
(12) antiparkinsonian drugs: amantadine HCl, promethazine HCl, metixene HCl, etc.;
(13) other agents acting on circulatory organs: diltiazem HCl, trimetazidine HCl, etc.;
(14) hypotensives: dihydroergotoxin mesilate, clonidine HCl, etc.;
(15) enzyme preparations: urokinase, hyaluronidase, etc.;
(16) others: naphazoline HCl, meclofenoxate HCl, methylephedrine HCl, homatropine hydrobromide, etc.

The relative proportions of the ingredients in the microemulsion of the invention are indicated below in terms of the ratio of water to each ingredient on a volume basis.

The ratio of water to surfactant ranges from 1:2 to 1:200, preferably from 1:3 to 1:20.

The ratio of water to oil component ranges from 1:3 to 1:5,000, preferably from 1:6 to 1:5,000.

The drug-containing microemulsion thus prepared is formulated in various dosage forms for absorption through either the skin or mucous membranes or peroral administration and common pharmaceutical formulation procedures may be employed as described below.

For absorption through the mucous membranes:

a) nasal drug: a spray container for nasal application is filled with the microemulsion, which is to be sprayed over the nasal mucosa;

b) rectal suppository: a suitable heat-fusible material such as polyethylene glycol which is not soluble in oils is heated to melt and fed into a mold to form a hollow shell, which is filled with the microemulsion. The opening in the shell is closed with a melt of the same heat-fusible material, whereby the microemulsion is confined in the closed shell. The thus prepared suppository is inserted into the rectum for actual use.

Alternatively, an oleaginous base that melts within the rectum is used as an oil component and while it is molten, water is added and the ingredients are mixed under agitation to form a microemulsion, which is cooled to solidify to a suppository form. The thus prepared suppository is inserted into the rectum for actual use.

For peroral administration:

The body of a hard gelatic capsule is filled with the microemulsion and slipped on a cap, with a gelatin solution being applied to the junction to form a barrier against leakage of the drug. After drying, the capsule is coated with an enteric substance such as hydroxypropylmethyl cellulose phthalate (HPMC) to formulate an enteric preparation, which is subsequently dried and administered perorally as required.

The hard gelatin capsule may be replaced by a soft gelatin capsule.

The following examples and experimental data are provided for the purpose of further illustrating the invention.

EXAMPLE 1

| Di-2-ethylhexylsulfosuccinic acid sodium (surfactant 1) | 7 g |
| --- | --- |
| Monooleic acid diglyceryl ester (HLB = 5.5) (surfactant 2) | 5 g |
| Isotonic phosphate buffer solution (aqueous component) | 2 g |
| Calcitonin (drug) | 5 mg |
| Trialiphatic acid ($C_8$–$C_{10}$) glyceryl ester (oil component) | to make 100 g |

To about 90% of the oil component, surfactant 1 [in class (a)] and surfactant 2 [in class (b)] were added and stirred thoroughly. In a separate step, calcitonin was dissolved in the aqueous component. The aqueous solution of calcitonin was added to the stirred mixture of the oil component and the surfactants. Further stirring gave a clear liquid. Under continued stirring, the remainder of the oil component was added to make a total volume of 100 g.

The thus prepared liquid was subjected to measurement with a laser light scattering particle size analyzer (Model DLS700 of Ohtsuka Denshi K.K.; Ar laser; maximum output, 15 mW) and it was found to be a W/O microemulsion having an average particle size of 14 nm.

EXAMPLE 2

| Polyoxyethylene hardened castor oil (EO = 40; HLB = 12.5) (surfactant 1) | 8 g |
| --- | --- |
| Monooleic acid diglyceryl ester (HLB = 5.5) (surfactant 2) | 8 g |
| Isotonic phosphate buffer solution containing bovin serum albumin (aqueous component) | 1 g |
| Erythropoietin (drug) | 1.25 mg |
| Trialiphatic acid ($C_8$–$C_{10}$) glyceryl ester (oil component) | to make 100 g |

To about 90% of the oil component, surfactant 1 [in class (b)] and surfactant 2 [in class (c)] were added and stirred thoroughly. Surfactant 1, which was semi-solid at room temperature, was heated during the agitation. In a separate step, erythropoietin was dissolved in the aqueous component. The mixture of the oil component and the surfactants was cooled to room temperature and the aqueous solution of erythropoietin was added to the stirred mixture. Further stirring gave a clear liquid. Under continued stirring, the remainder of the oil component was added to make a total volume of 100 g.

The thus prepared liquid was subjected to measurement with a laser light scattering particle size analyzer (Model 370 of NICOMP Inc.; Ar laser; maximum output, 70 mW) and it was found to be a W/O microemulsion having an average particle size of 30 nm.

EXAMPLE 3

| Polyoxyethylene (20 moles) hardened castor oil (HLB = 10.5) (surfactant 1) | 4 g |
| --- | --- |
| Polyoxyethylene (10 moles) hardened castor oil (HLB = 6.5) (surfactant 2) | 10 g |
| Isotonic phosphate buffer solution (aqueous component) | 1 g |
| Alpha-interferon (drug) | 500 μg |
| Soybean oil (oil component) | to make 100 g |

To about 90% of the oil component, surfactant 1 [in class (b)] and surfactant 2 [in class (c)] were added and stirred thoroughly. In a separate step, the interferon was dissolved in the aqueous component. The aqueous solution of interferon was added to the stirred mixture of the oil component and the surfactants. Further, stirring gave a clear liquid. Under continued stirring, the remainder of the oil component was added to make a total volume of 100 g.

The thus prepared liquid was subjected to measurement with a laser light scattering particle size analyzer (Model 370 of NICOMP Inc., see supra) and it was found to be a W/O microemulsion having an average particle size of 30 nm.

EXAMPLE 4

| | |
|---|---|
| Calcitonin (drug) | 2.0 mg |
| Isotonic phosphate buffer solution (aqueous component) | 1 ml |
| Sorbitan monooleate POE (20) (HLB = 15.0) (surfactant 1) | 2.0 g |
| Monooleic acid diglyceryl ester (HLB = 5.5) (surfactant 2) | 10.0 g |
| Middle-chain aliphatic acid triglyceride (oil component) | 100 ml in total |

Calcitonin was dissolved in the aqueous component. Surfactant 1 [in class (b)] and surfactant 2 [in class (c)] were added to 80% of the oil component and the ingredients were stirred to form a solution. The calcitonin solution was added to the oil component having the surfactants dissolved therein and the mixture was stirred. Continued stirring gave a clear microemulsion, to which the remainder of the oil component was added to make a total volume of 100 ml. The resulting liquid was subjected to measurement with a laser light scattering particle size analyzer (Model DLS-7000 of Oht-suka Denshi K.K.; Ar laser; maximum output, 75 mW) and it was found to be a very fine microemulsion having an average particle size of 2.4 nm.

A mixture of this microemulsion with water was subjected to ultra centrifugation and the content of calcitonin in the resulting aqueous phase was determined; 92% of the calcitonin added to make the microemulsion could be recovered (when 1 g of calcitonin was added, a total of 0.92 g could be recovered).

EXAMPLE 5

| | |
|---|---|
| G-CSF (drug) | 500 μg |
| Isotonic phosphate buffer solution (aqueous component) | 1 ml |
| Di-2-ethylhexylsulfosuccinic acid sodium (surfactant 1) | 7.0 g |
| Monooleic acid diglyceryl ester (HLB = 5.5) (surfactant 2) | 5.0 g |
| Middle-chain aliphatic acid triglyceride (oil component) | 100 ml |

G-CSF was dissolved in the aqueous component. Surfactant 1 [in class (a)] and surfactant 2 [in class (c)] were added to 80% of the oil component and the ingredients were stirred to form a solution. The G-CSF solution was added to the oil component having the surfactants dissolved therein and the mixture was stirred. Continued stirring gave a clear microemulsion, to which the remainder of the oil component was added to make a total volume of 100 ml. The resulting liquid was subjected to measurement with a laser light scattering particle size analyzer (Model DLS-7000 of Oht-suka Denshi K.K., see supra) and it was found to be a very fine microemulsion having an average particle size of 6.5 nm.

A mixture of this microemulsion with water was subjected to ultra centrifugation and the content of G-CSF in the resulting aqueous phase was determined; 89% of the G-CSF added to make the microemulsion could be recovered.

EXAMPLE 6

| | |
|---|---|
| G-CSF (drug) | 500 μg |
| Isotonic phosphate buffer solution (aqueous component) | 1 ml |
| Polyoxyethylene (9) lauryl ether (HLB = 14.5) (surfactant 1) | 10.0 g |
| Sorbitan sesquioleate (HLB = 3.7) (surfactant 2) | 2.0 g |
| Middle-chain aliphatic acid triglyceride (oil component) | 100 ml in total |

G-CSF was dissolved in the aqueous component. Surfactant 1 [in class (b)] and surfactant 2 [in class (c)] were added to 80% of the oil component and the ingredients were stirred to form a solution. The G-CSF solution was added to the oil component having the surfactants dissolved therein and the mixture was stirred. Continued stirring gave a clear microemulsion, to which the remainder of the oil component was added to make a total volume of 100 ml. The resulting liquid was subjected to measurement with a laser light scattering particle size analyzer (Model DLS-7000 of Oht-suka Denshi K.K., see supra) and it was found to be a microemulsion having an average particle size of 44 nm.

A mixture of this microemulsion with water was subjected to ultra centrifugation and the content of G-CSF in the resulting aqueous phase was determined; 86% of the G-CSF added to make the microemulsion could be recovered.

EXAMPLE 7

| | |
|---|---|
| Carbenicillin sodium (drug) | 400 mg |
| Distilled water (aqueous component) | 1.0 ml |
| Sorbitan monooleate polyoxyethylene (20) (HLB = 15.0) (surfactant 1) | 2.0 g |
| Sorbitan sesquioleate (HLB = 3.7) (surfactant 2) | 10.0 g |
| Middle-chain aliphatic acid triglyceride (oil component) | 100 ml in total |

Carbenicillin was dissolved in the aqueous component. Surfactant 1 [in class (b)] and surfactant 2 [in class (c)] were added to 80% of the oil component and the ingredients were stirred to form a solution. The carbenicillin solution was added to the oil component having the surfactants dissolved therein and the mixture was stirred. Continued stirring gave a clear microemulsion, to which the remainder of the oil component to make a total volume of 100 ml. The resulting liquid was subjected to measurement with a laser light scattering particle size analyzer (Model DLS-7000 of Oht-suka Denshi K.K., see supra) and it was found to be a microemulsion having an average particle size of 9.2 nm.

EXAMPLE 8

| | |
|---|---|
| Antipyrine (drug) | 200 mg |
| Distilled water (water component) | 1 ml |
| Di-2-ethylhexylsulfosuccinic acid sodium (surfactant 1) | 7.0 g |
| Monooleic acid diglyceryl ester (HLB = 5.5) (surfactant 2) | 5.0 g |
| Middle-chain aliphatic acid triglyceride (oil component) | 100 ml in total |

Antipyrine was dissolved in the aqueous component. Surfactant 1 [in class (a)] and surfactant 2 [in class (c)] were added to 80% of the oil component and the ingredients were stirred to form a solution. The antipyrine solution was added to the oil component having the surfactants dissolved therein and the mixture was stirred. Continued stirring gave a clear microemulsion, to which the remainder of the oil component was added to make a total volume of 100 ml.

EXAMPLE 9

| Propantheline bromide (drug) | 100 mg |
|---|---|
| Distilled water (aqueous component) | 1 ml |
| Di-2-ethylhexylsulfosuccinic acid sodium (surfactant 1) | 7.0 g |
| Monooleic acid diglyceride (HLB = 5.5) (surfactant 2) | 5.0 g |
| Middle-chain aliphatic acid triglyceride (oil component) | 100 ml in total |

Propantheline bromide was dissolved in the aqueous component. Surfactant 1 [in class (a)] and surfactant 2 [in class (c)] were added to 80% of the oil component and the ingredients were stirred to form a solution. The propantheline bromide solution was added to the oil component having the surfactants dissolved therein and the mixture was stirred. Continued stirring gave a clear microemulsion, to which the remainder of the oil component was added to make a total volume of 100 ml.

EXAMPLE 10

| Procainamide HCl (drug) | 400 mg |
|---|---|
| Distilled water (aqueous component) | 1.0 ml |
| Polyoxyethylene (9) lauryl ether (HLB = 14.5) (surfactant 1) | 10.0 g |
| Sorbitan sesquioleate (HLB = 3.7) (surfactant 2) | 2.0 g |
| Middle-chain aliphatic acid triglyceride (oil component) | 100 ml in total |

Procainamide HCl was dissolved in the aqueous component. Surfactant 1 [in class (b)] and surfactant 2 [in class (c)] were added to 80% of the oil component and the ingredients were stirred to form a solution. The procainamide HCl solution was added to the oil component having the surfactants dissolved therein and the mixture was stirred. Continued stirring gave a clear microemulsion, to which the middle-chain aliphatic acid triglyceride was added to make a total volume of 100 ml.

EXAMPLE 11

| Riboflavin phosphate sodium (drug) | 10 mg |
|---|---|
| Distilled water (aqueous component) | 1 ml |
| Di-2-ethylhexylsulfosuccinic acid sodium (surfactant 1) | 7.0 g |
| Monooleic acid diglyceryl ester (HLB = 5.5) (surfactant 2) | 5.0 g |
| Middle-chain aliphatic acid triglyceride (oil component) | 100 ml in total |

Riboflavin phosphate sodium was added to the aqueous component and the ingredients were stirred to form a solution. Surfactant 1 [in class (a)] and surfactant 2 [in class (c)] were added to the oil component and the ingredients were stirred to form a solution, to which the riboflavin phosphate sodium solution was added and the mixture was stirred. Continued stirring gave a clear, pale yellow microemulsion.

EXAMPLE 12

| Amaranth (model compound) | 1 mg |
|---|---|
| Distilled water (aqueous component) | 1 ml |
| Sodium dodecylsulfate (surfactant 1) | 4.0 g |
| Monooleic acid diglyceryl ester (HLB = 5.5) (surfactant 2) | 6.0 g |
| Middle-chain aliphatic acid triglyceride (oil component) | 100 ml in total |

A red pigment Amaranth* was dissolved as a model compound (drug substitute) in water. Surfactants 1 and 2 were added to 80% of the oil component and the mixture was stirred for 60 min to prepare a dispersion of the surfactants. The aqueous component having Amaranth dissolved therein was added to the oil component having the surfactants dispersed therein and the mixture was stirred for 80 min. Upon standing, a supernatant formed and it was collected and centrifuged at 7000 rpm for 40 min to give a clear liquid. This liquid was subjected to measurement with a laser light scattering particle size analyzer (Model DLS-7000 of Ohtsuka Denshi K.K., see supra) and it was found to have an average particle size of 52 nm. The volume of this liquid was doubled by addition of water and upon super-high-speed centrifugation at 5000 rpm for 1.5 h, a slightly red aqueous phase formed.

* Amaranth:
3-hydroxy-4-[(4-sulfo-1-naphthalenyl)azo]-2,7-naphthalenedisulfonic acid trisodium salt Experiment on the Absorbability of Drug-Containing Emulsions (Methods)

(1) Absorption through the skin:

A piece of lint (3×4 cm) lined with a polyethylene sheet (4×5 cm) was coated uniformly with 0.4–0.7 ml of the drug-containing microemulsion prepared in Example 1 or 2. Rats were shaven on the back, to which the lint and a stretchable bandage were applied in that order. Blood was sampled from the rats at specified time intervals and the concentration of the drug in the blood was determined.

(2) Absorption by the alimentary tract:

Rats were incised in the abdomen and a silicone rubber tube was passed through the alimentary tract from the stomach wall to the duodenum, followed by suturing of the stomach wall, peritoneum and skin through which the tube penetrated. After the rats recovered from the operative invasion, the drug-containing microemulsion prepared in Example 1 or 2 was administered via the silicone rubber tube, which was then closed. As in (1), blood was sampled at specified time intervals and the concentration of the drug in the blood was determined.

(3) Absorption by the rectum (through the mucous membrane):

Rats were starved from the day before experiment until there was little feces left in the abdomen. Then, a rubber band was applied to the anus of each animal, through which a tube was inserted for injecting a predetermined amount of the drug-containing microemulsion prepared in Example 1 or 2. Immediately after the injection, the anus was bound with a rubber band to prevent the leakage of the microemulsion. Blood was sampled at specified time intervals and the concentration of the drug in the blood was determined.

(4) Administration into the nasal cavity:

Administration into the nasal cavity was performed by a closure technique in accordance with the method of Hirai et al. (INTERNATIONAL JOURNAL OF PHARMACEUTICS, 7 (1981) 317–325). Rats were anesthetized and medisected in the neck to expose the windpipe and esophagus. Part of the windpipe was incised and a polyethylene tube was inserted into the windpipe to secure the airway, followed by ligation. The nostril and the opening in the incisive caval on the oral cavity side were closed with an adhesive. Part of the esophagus was incised for insertion of a nutrition catheter until its end reached into the nasal cavity. The part of the esophagus into which the nutrition catheter was inserted was ligated. The drug-containing microemulsion prepared in Example 1 or 2 was injected into the animals via the nutrition catheter. Blood was sampled at specified time intervals and the change in the concentration of the drug in the blood was determined over time.

(Results)

The data on the absorption of the microemulsions prepared in accordance with the invention are shown in Table 1 for three different routes, transdermic, peroral (by the alimentary tract) and permucosal (or by the rectum).

None of the microemulsions tested caused local irritation in any regions including the skin and mucous membranes.

TABLE 1

|  | Microemulsion | | Availability* Site of administration | | | |
|---|---|---|---|---|---|---|
| Peptide | Surfactant | Example | Duodenum | Skin | Rectum | Nasal cavity |
| EPO | a + c | 1(*1) | 2.6% | 1.2% | 1.7% | — |
|  | b + c | 2 | 1.1% | — | — | — |
| Calcitonin | a + c | 1 | 2.3% | 3.5% | 22.5% | 50% |

Availability: Relative value with the availability upon subcutaneous injection (i.e., integrated blood concentration over time) being taken as 100%.
(*1)According to Example 1, except that calcitonin was replaced by erythropoietin.

(Evaluation of the Experimental Data)

For macromolecular peptides such as erythropoietin, availability values of 2–3% are remarkable. Speaking of calcitonin, the availability 22–23% due to rectal absorption and the value 50% due to absorption by the nasal cavity are both satisfactory for practical purposes.

We claim:

1. A water-in-oil microemulsion preparation containing a slightly absorbable physiologically active substance in an aqueous phase comprising a trialiphatic $C_8$–$C_{10}$ glyceryl ester, said microemulsion consisting essentially of an oil phase, an aqueous phase and a combination of surfactants, said oil phase comprising trialiphatic $C_8$–$C_{10}$ glyceryl ester as the dispersion medium said combination of surfactants consisting essentially of at least one surfactant in class (c) in combination with at least one surfactant in class (a) or class (b), wherein said classes of surfactants are:

(a) an ionic surfactant selected from the group consisting of di-2-ethylhexylsulfosuccinic acid sodium and sodium dodecylsulfate;

(b) a nonionic surfactant with an HLB of 10–20 selected from the group consisting of a polyoxyethylene-added hardened castor oil containing an average of 40 to 60 moles of oxyethylene in the polyoxyethylene moiety, sodium monooleate polyoxyethylene wherein the polyoxyethylene moiety contains an average of 10–40 moles of ethylene glycol, and a polyoxyethylene lauryl ether, wherein the polyoxyethylene moiety has 4 to 25 moles of oxyethylene; and (c) a nonionic surfactant with an HLB of from 3 to 7 selected from the group consisting of, monooleic acid diglyceryl ester, sorbitan sesquioleate and a polyoxyethylene-added hardened castor oil having an average of from 8 to 12 moles of oxyethylene in the polyoxyethylene moiety;

wherein the particle size of the particles in the microemulsion is 0.4–100 nanometers as determined by a laser light scattering particle size analyzer.

2. A microemulsion preparation according to claim 1 wherein the slightly absorbable physiologically active substance is selected from the group consisting of vasopressin, calcitonin, erythropoietin, colony-stimulating factor, interleukins, interferons, insulin, and accessory thyroid hormone.

3. A microemulsion preparation according to claim 1 wherein the slightly absorbable physiologically active substance is selected from the group consisting of vasopressin, calcitonin, erythropoietin, colony-stimulating factor, interleukins, interferons, insulin, and accessory thyroid hormone.

4. A microemulsion preparation according to claim 2 wherein the slightly absorbable physiologically active substance is selected from the group consisting of vasopressin, calcitonin, erythropoietin, colony-stimulating factor, interleukins, interferons, insulin, and accessory thyroid hormone.

5. A microemulsion preparation according to claim 1 which is formulated in a dosage form suitable for transdermic, peroral or transmucosal administration.

* * * * *